(12) United States Patent
Brister

(10) Patent No.: US 8,435,286 B2
(45) Date of Patent: May 7, 2013

(54) STENT WITH INTERMITTENT COATING

(75) Inventor: Mark Brister, Encinitas, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 680 days.

(21) Appl. No.: 10/531,822

(22) PCT Filed: Oct. 14, 2003

(86) PCT No.: PCT/US03/32441
§ 371 (c)(1),
(2), (4) Date: Oct. 24, 2005

(87) PCT Pub. No.: WO2004/037443
PCT Pub. Date: May 6, 2004

(65) Prior Publication Data
US 2006/0155370 A1      Jul. 13, 2006

Related U.S. Application Data

(60) Provisional application No. 60/420,685, filed on Oct. 22, 2002.

(51) Int. Cl.
*A61F 2/82*      (2006.01)
(52) U.S. Cl.
USPC ........................................ 623/1.42; 623/1.46
(58) Field of Classification Search ................. 623/1.11, 623/1.1, 1, 15, 1.15, 1.39–1.46; 606/192–194; 604/96.01, 48, 500, 507, 508, 509
See application file for complete search history.

(56) References Cited

U.S. PATENT DOCUMENTS

| | | | |
|---|---|---|---|
| 4,739,762 A | 4/1988 | Palmaz | |
| 5,133,732 A | 7/1992 | Wiktor | |
| 5,292,331 A * | 3/1994 | Boneau | 623/1.16 |
| 5,383,928 A | 1/1995 | Scott et al. | |
| 5,421,955 A | 6/1995 | Lau et al. | |
| 5,873,904 A * | 2/1999 | Ragheb et al. | 623/1.13 |
| 6,090,127 A | 7/2000 | Globerman | |
| 6,096,070 A * | 8/2000 | Ragheb et al. | 623/1.39 |
| 6,129,705 A | 10/2000 | Grantz | |

(Continued)

FOREIGN PATENT DOCUMENTS

| | | |
|---|---|---|
| EP | 0701802 | 3/1996 |
| EP | 1329230 | 7/2003 |

(Continued)

*Primary Examiner* — Elizabeth Houston

(57) ABSTRACT

The stent with an intermittent coating of the present invention provides a coating having a plurality of discrete coating sections disposed on a stent, i.e., an intermittent coating. The individual coating sections can contain different drugs or therapeutic agents, can be made of different polymers, can be made with different solvents, or combinations thereof. The coating sections can be applied in patterns such as ring patterns, striped patterns, spotted patterns, or dot matrix patterns. In one embodiment, the regions can be large relative to the stent, such as a ring pattern including one therapeutic agent in the radial regions at the ends of a stent and a different therapeutic agent in the radial region in the middle. In another embodiment, the regions can be small relative to the stent, such as a dot matrix pattern with each grid region being a small point.

23 Claims, 7 Drawing Sheets

U.S. PATENT DOCUMENTS

| | | |
|---|---|---|
| 6,238,410 B1 | 5/2001 | Vrba et al. |
| 6,344,028 B1 | 2/2002 | Barry |
| 6,616,765 B1 * | 9/2003 | Castro et al. ............... 118/669 |
| 2002/0010505 A1 * | 1/2002 | Richter ....................... 623/1.15 |
| 2002/0051730 A1 | 5/2002 | Bodnar et al. |
| 2002/0133183 A1 | 9/2002 | Lentz et al. |
| 2003/0181973 A1 * | 9/2003 | Sahota ......................... 623/1.15 |

FOREIGN PATENT DOCUMENTS

| | | |
|---|---|---|
| WO | WO 98/56312 | 12/1998 |
| WO | WO 00/12147 | 3/2000 |
| WO | WO 01/87372 | 11/2001 |
| WO | WO 02/43619 | 6/2002 |
| WO | WO 02/074194 | 9/2002 |

* cited by examiner

STENT WITH INTERMITTENT COATING

TECHNICAL FIELD

The technical field of this disclosure is medical implant devices, particularly, a stent having an intermittent coating.

BACKGROUND OF THE INVENTION

Stents are generally cylindrical shaped devices that are radially expandable to hold open a segment of a blood vessel or other anatomical lumen after implantation into the body lumen. Stents have been developed with coatings to deliver drugs or other therapeutic agents.

Stents are used in conjunction with balloon catheters in a variety of medical therapeutic applications including intravascular angioplasty. For example, a balloon catheter device is inflated during PTCA (percutaneous transluminal coronary angioplasty) to dilate a stenotic blood vessel. The stenosis may be the result of a lesion such as a plaque or thrombus. After inflation, the pressurized balloon exerts a compressive force on the lesion thereby increasing the inner diameter of the affected vessel. The increased interior vessel diameter facilitates improved blood flow. Soon after the procedure, however, a significant proportion of treated vessels re-narrow.

To prevent restenosis, short flexible cylinders, or stents, constructed of metal or various polymers are implanted within the vessel to maintain lumen size. The stents acts as a scaffold to support the lumen in an open position. Various configurations of stents include a cylindrical tube defined by a mesh, interconnected stents or like segments. Some exemplary stents are disclosed in U.S. Pat. No. 5,292,331 to Boneau, U.S. Pat. No. 6,090,127 to Globerman, U.S. Pat. No. 5,133,732 to Wiktor, U.S. Pat. No. 4,739,762 to Palmaz and U.S. Pat. No. 5,421,955 to Lau. Balloon-expandable stents are mounted on a collapsed balloon at a diameter smaller than when the stents are deployed. Stents can also be self-expanding, growing to a final diameter when deployed without mechanical assistance from a balloon or like device.

Stents have been used with coatings to deliver drug or other therapy at the site of the stent. The coating can be applied as a liquid containing the drug or other therapeutic agent dispersed in a polymer/solvent matrix. The liquid coating then dries to a solid coating upon the stent The liquid coating can be applied by painting, spraying, dipping, wiping, electrostatic deposition, vapor deposition, epitaxial growth, combinations thereof, and other methods, including dipping or spraying the stent while spinning or shaking the stent to achieve a uniform coating. Combinations of the various application techniques can also be used.

The number of drugs suitable for use with stents in treating various pathologies in an artery or other body lumen is growing. New discoveries give rise to new drugs that may be effective in treating one or more pathologies present in a particular case. Although a combination of the drugs may be desirable to treat the different pathologies, the drugs, their preferred polymers, or the solvents required for application to a stent can be incompatible. The incompatibilities can both cause manufacturing problems and reduce the effectiveness of the therapeutic agents during use.

The compatibility problem can arise several ways in mixing more than one drug for application and use on a stent. First, the drugs themselves can be incompatible. Second, the drugs can have different solubility in a particular solvent, so that one drug dissolves easily, but the other drug is difficult to get into solution. In the extreme case, one drug may not be soluble in the preferred solvent for the other drug, so that two different solvents are required. In addition, the preferred polymer for one drug may be incompatible with the preferred polymer for the other drug. Needless to say, such factors can make the precise selection of materials difficult when two or more drugs are to be delivered. A uniform coating with different drugs contained in a single polymer can also limit the therapy options available. Although the preferred therapy may be to deliver one drug rapidly and another drug more slowly, both drugs are limited to their respective diffusion rates from the single polymer. In another case, it may be desirable to use a biodegradable polymer with one drug and a non-biodegradable polymer with another drug.

U.S. Pat. No. 5,383,928 to Scott et al. discloses a sheath for encompassing at least a portion of a stent to locally deliver a drug to an arterial wall or lumen into which the stent has been inserted, comprising a polymer and a drug incorporated within the polymer, the polymer sheath encompassing at least a portion of the stent and having a thickness to allow controlled release of the drug.

WIPO International Publication No. WO00/12147 to Yang et al. discloses a device adapted for mounting on a stent, the device comprising a sheath being made of polymeric material that includes drugs such as pharmaceutical agent(s) or radioactive agent(s) for delivery to an implant site. The sheath includes a main body of generally tubular shape, and may include mounting means for attaching same to stent. The device may have a slit therein, and may comprise a helical coil, a cylinder or any other suitable shape or design which fits a particular stent. The sheath may include a coating or coatings thereon containing drugs, surgical adhesives or a combination thereof.

It would be desirable to have a stent having an intermittent coating that would overcome the above disadvantages.

SUMMARY OF THE INVENTION

One aspect of the present invention provides a stent having an intermittent coating able to provide various therapies from a single stent.

Another aspect of the present invention provides a stent having an intermittent coating to allow use of a plurality of drugs or therapeutic agents over a single stent.

Another aspect of the present invention provides a stent having an intermittent coating to allow use of a plurality of polymers over a single stent.

Another aspect of the present invention provides a stent having an intermittent coating manufactured through use of solvents most compatible with a particular drug and polymer combination.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

DETAILED DESCRIPTION OF THE PRESENTLY PREFERRED EMBODIMENT

The stent with an intermittent coating of the present invention provides a coating having a plurality of discrete coating sections disposed on a stent, i.e., an intermittent coating. The individual coating sections can contain different drugs or therapeutic agents, can be made of different polymers, can be made with different solvents, or combinations thereof. The coating sections can be applied in patterns such as ring patterns, striped patterns, spotted patterns, or dot matrix patterns. In one embodiment, the regions can be large relative to the stent, such as a ring pattern including one therapeutic agent in the radial regions at the ends of a stent and a different therapeutic agent in the radial region in the middle. In another embodiment, the regions can be small relative to the stent, such as a dot matrix pattern with each grid region being a small point.

Figure 1:
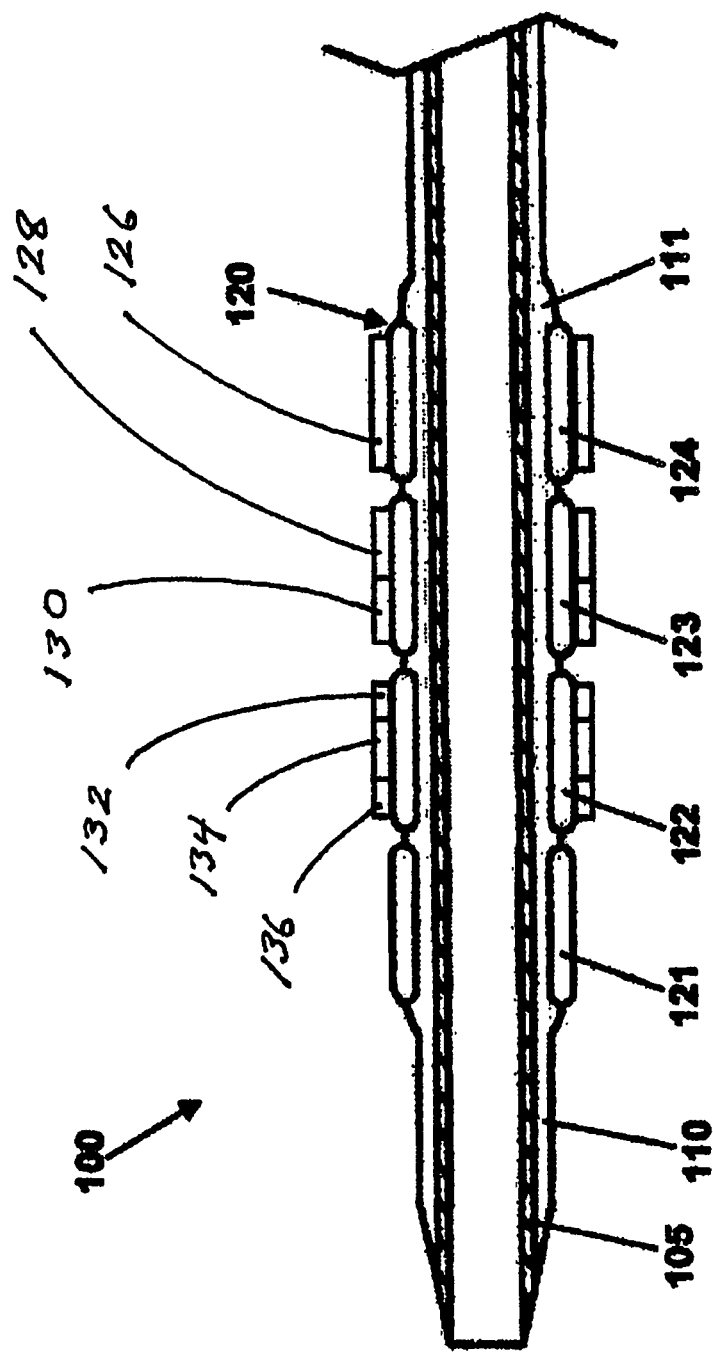
FIG. 1 shows a stent delivery system made in accordance with the present invention.

FIG. 1 shows a stent delivery system made in accordance with the present invention. The stent delivery system 100 includes a catheter 105, a balloon 110 operably attached to the catheter 105, and a stent 120 disposed on the balloon 110. The balloon 110, shown in a collapsed state, may be any variety of balloons capable of expanding the stent 120. The balloon 110 may be manufactured from any sufficiently elastic material such as polyethylene, polyethylene terephthalate (PET), nylon, or the like. In one embodiment, the balloon 110 may include retention means 111, such as mechanical or adhesive structures, for retaining the stent 120 until it is deployed. The catheter 105 may be any variety of balloon catheters, such as a PTCA (percutaneous transluminal coronary angioplasty) balloon catheter, capable of supporting a balloon during angioplasty.

The stent 120 may be any variety of implantable prosthetic devices capable of carrying a coating known in the art. In one embodiment, the stent 120 may have a plurality of identical cylindrical stent segments placed end to end. Four stent segments 121, 122, 123, and 124 are shown, and it will be recognized by those skilled in the art that an alternate number of stent segments may be used.

The stent segments can be provided with one or more discrete coating sections as desired. Stent segment 121 is shown without a coating. Coating section 126 is disposed on stent segment 124, coating sections 128 and 130 are disposed on stent segment 123, and coating sections 132, 134, and 136 are disposed on stent segment 122. The different coatings can be made of the same material or different materials, and can contain the same therapeutic agents or different therapeutic agents. The coatings can be applied as a liquid polymer/solvent matrix. The liquid coating can be applied to the stent 120 by pad printing, inkjet printing, rolling, painting, spraying, micro-spraying, dipping, wiping, electrostatic deposition, vapor deposition, epitaxial growth, combinations thereof, and other methods as will be appreciated by those skilled in the art. A therapeutic agent can be incorporated in the coating, or can be omitted and the coating included for its mechanical or biological properties alone.

The coatings are merely exemplary, and it should be recognized that other coating configurations, such as multiple coating layers, are possible. Although the coatings are shown schematically on the outer circumference of the stent 120, the coatings can coat the whole stent 120, both inside and outside, and around the cross section of individual stent wires.

The coating can be a polymer including, but not limited to, urethane, polyester, epoxy, polycaprolactone (PCL), polymethylmethacrylate (PMMA), PEVA, PBMA, PHEMA, PEVAc, PVAc, Poly N-Vinyl pyrrolidone, Poly (ethylene-vinyl alcohol), combinations of the above, and the like. Suitable solvents that can be used to form the liquid coating include, but are not limited to, acetone, ethyl acetate, tetrahydrofuran (THF), chloroform, N-methylpyrrolidone (NMP), phosphorylcholine, combinations of the above, and the like. Suitable therapeutic agents include, but are not limited to, antiangiogenesis agents, antiendothelin agents, antimitogenic factors, antioxidants, antiplatelet agents, antiproliferative agents, antisense oligonucleotides, antithrombogenic agents, calcium channel blockers, clot dissolving enzymes, growth factors, growth factor inhibitors, nitrates, nitric oxide releasing agents, vasodilators, virus-mediated gene transfer agents, agents having a desirable therapeutic application, combinations of the above, and the like. Specific example of therapeutic agents include abciximab, angiopeptin, colchicine, eptifibatide, heparin, hirudin, lovastatin, methotrexate, rapamycin, Resten-NG (AVI-4126) antisense compound, streptokinase, taxol, ticlopidine, tissue plasminogen activator, trapidil, urokinase, and growth factors VEGF, TGF-beta, IGF, PDGF, and FGF.

Figure 2:
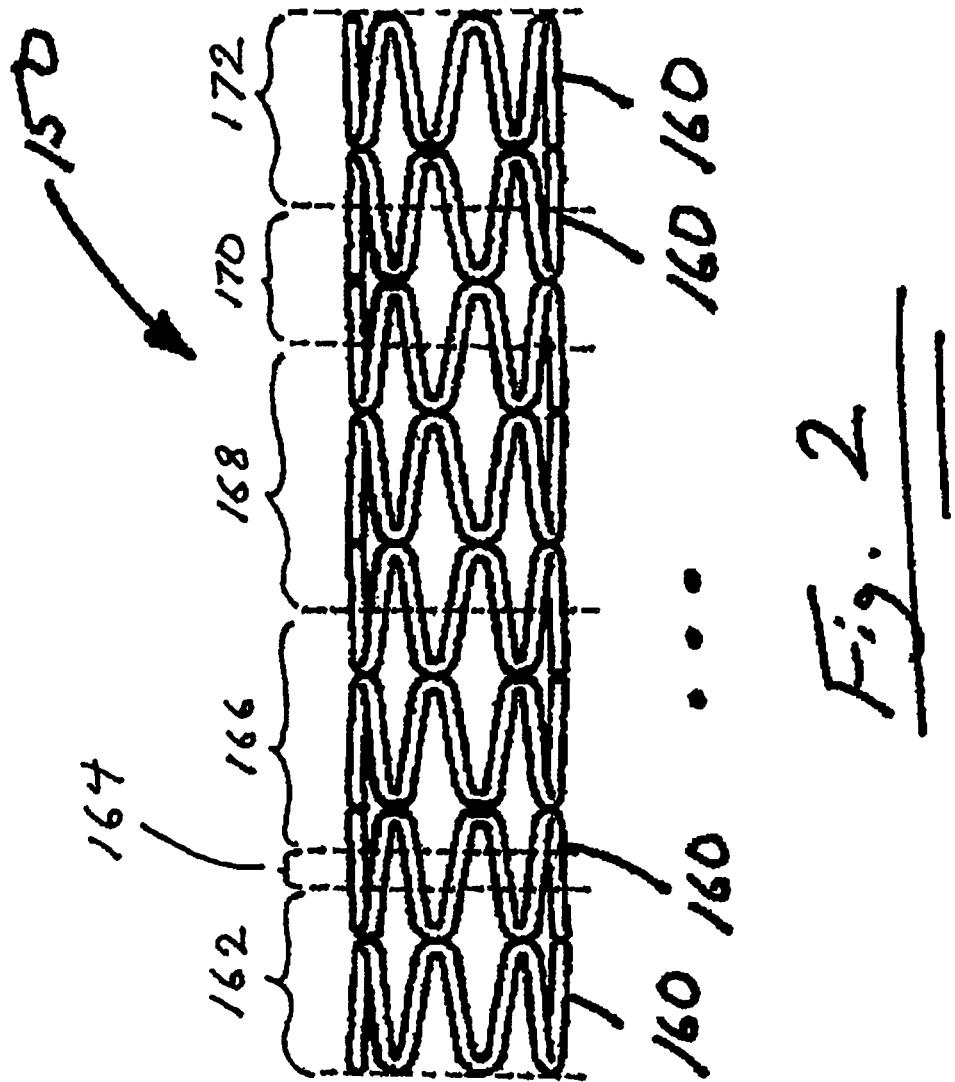
FIGS. 2-5 show exemplary embodiments of a stent having an intermittent coating made in accordance with the present invention.

FIG. 2 shows a stent having an intermittent coating made in accordance with the present invention. The stent 150 comprises a number of segments 160. The pattern of the stent segments 160 can be W-shaped or can be a more complex shape with the elements of one segment continuing into the adjacent segment. The stent 150 can be installed in the stent delivery system of FIG. 1 for implantation in a body lumen.

Referring to FIG. 2, the stent 150 is conventional to stents generally and can be made of a wide variety of medical implantable materials, such as stainless steel particularly 316-L stainless steel or 316LS), MP35N alloy, nitinol, tantalum, ceramic, nickel, titanium, aluminum, polymeric materials, tantalum, MP35N, titanium ASIM F63-83 Grade 1, niobium, high carat gold K 19-22, and combinations thereof. The stent 150 can be formed through various methods as well. The stent 150 can be welded, laser cut, molded, or consist of filaments or fibers which are wound or braided together in order to form a continuous structure. Depending on the material, the stent can be self-expanding, or can be expanded by a balloon or some other device. The stent can be bare, or can have one or more uniform coatings over the stent to provide specific therapies, protect underlying layers, or promote coating adherence.

A coating with discrete intermittent coating sections can be on the surface of the stent segments 160. An individual coating section can be placed on the stent where the particular therapy provided by the individual coating section is appropriate The example of FIG. 2 shows the coating sections as a ringed pattern within radial regions on the stent 150. The coating sections within the radial regions 162 and 172 cross two stent segments, one of which is an end segment. The coating section within the radial region 164 is disposed on a single stent segment. The coating sections within the radial regions 166 and 168 cross several stent segments. The coating section within the radial region 170 crosses the region where two segments join. Different therapeutic agents can be included in the coating section within each discrete radial region, although the same therapeutic agents can be included in some of the coating sections, if desired. For example, a therapeutic agent could be provided at the ends of the stent to assist in the healing of edge dissection. A therapeutic agent such as taxol could be included in coating sections within the end radial regions 162 and 172, and a different therapeutic agent such as rapamycin included in coating sections within the middle radial regions 164, 166, 168, and 170.

Figure 3:
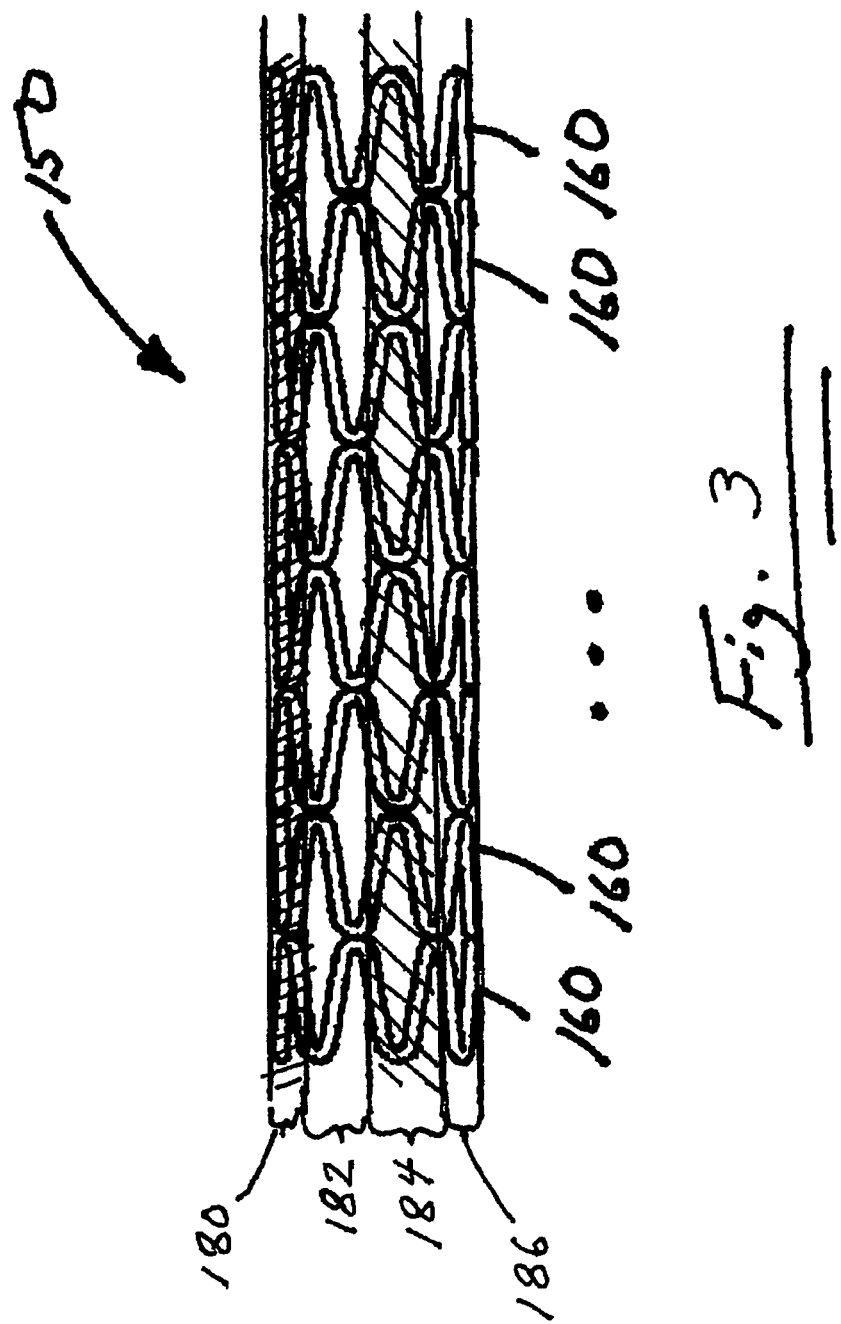
Figure 4:
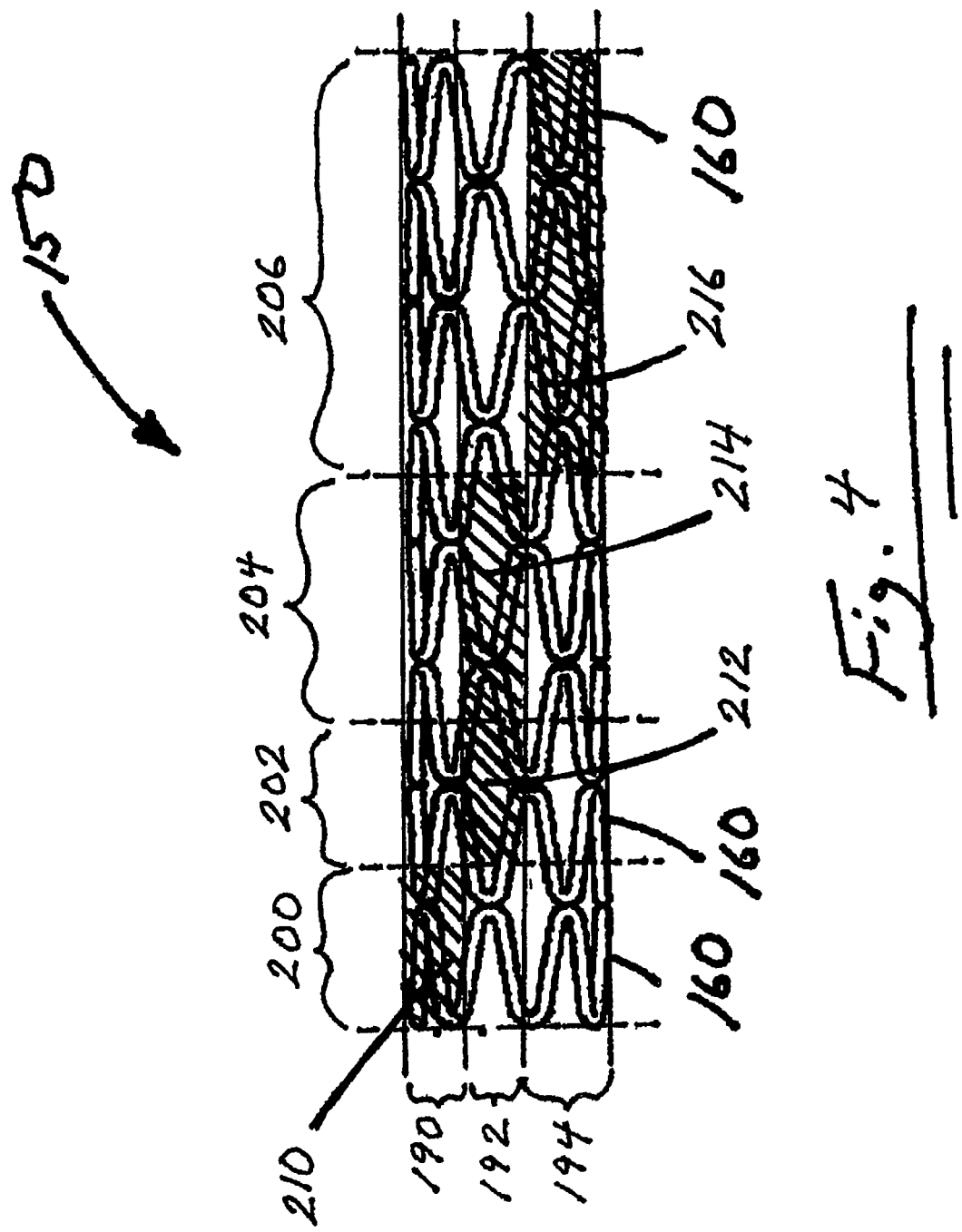

The coating sections can be disposed on the stent in a variety of patterns. FIGS. 3 & 4 show examples of a striped pattern and a spotted pattern, respectively. The examples show the patterns as large relative to the stent, however, those skilled in the art will appreciate that the pattern can be made larger or smaller as desired to suit a particular application.

FIG. 3, in which like elements share like reference numbers with FIG. 2, shows another embodiment of a stent having an intermittent coating made in accordance with the present invention. Different coating sections can be provided in the longitudinal regions 180, 182, 184, and 186 to form a striped pattern parallel to the axis of stent 150. Different therapeutic agents can be included in the coating section within each discrete radial region, although the same therapeutic agents can be included in some of the coating sections, if desired.

FIG. 4, in which like elements share like reference numbers with FIGS. 2 & 3, shows another embodiment of a stent having an intermittent coating made in accordance with the present invention. Different coating sections can be provided in the grid regions defined by the intersection of the radial regions 190, 192, and 194 and the longitudinal regions 200, 202, 204, and 206 to form a spotted pattern. Different therapeutic agents can be included in the coating section within each discrete grid region, although the same therapeutic agents can be included in some of the coating sections, if desired. Referring to FIG. 4, the coating sections in grid regions 210, 212, 214, and 216 are shown as having different coating sections from the other grid regions, as indicated by the hatched areas over grid regions 210, 212, 214, and 216. The coating sections in the grid regions 210, 212, 214, and 216 can differ from the coating sections in the other grid regions in various characteristics, such as polymer, therapeutic agent, solvent used, or combinations thereof. The grid regions are shown in a large size relative to the stent size for example only: those skilled in the art will appreciate that the grid size can be reduced to hundredths of a millimeter as possible in micro-sprayer and inkjet technology to produce fine detail in the pattern of the coating section.

Figure 5:
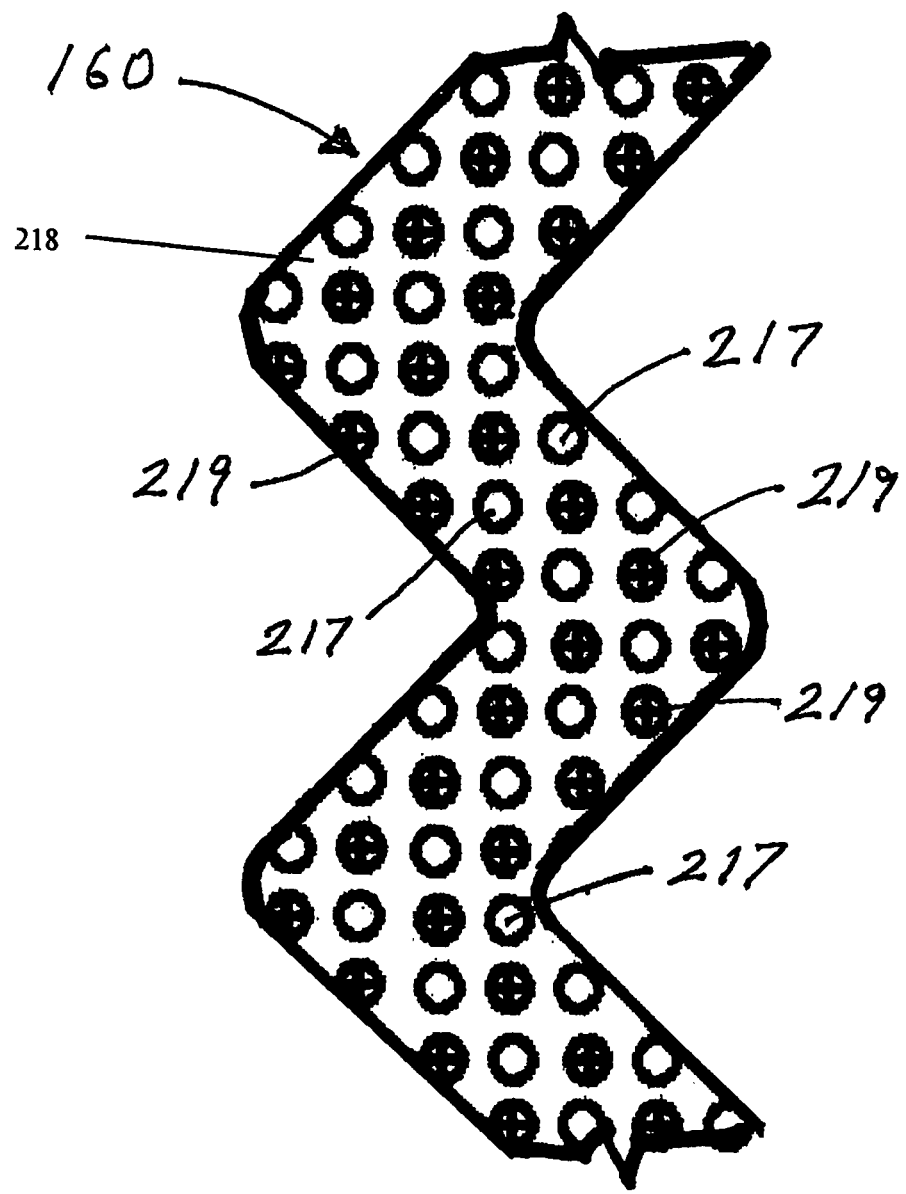

FIG. 5 shows a detail view of one embodiment of a stent having an intermittent coating made in accordance with the present invention. The grid regions are a very small size in this embodiment, so that the spotted pattern becomes a dot matrix pattern with space between the individual spots. First coating section 217 and second coating section 219 are disposed on the stent segment 160. In one embodiment, the first coating section 217 and second coating section 219 can include different therapeutic agents. In another embodiment, the first coating section 217 and second coating section 219 can include the same therapeutic agents within a macroscopic radial, longitudinal, or grid region. The first coating section 217 and second coating section 219 can differ in other characteristics besides therapeutic agents, such as being different polymers or being manufactured using different solvents. Those skilled in the art will appreciate that the individual coating segments shown as dots in the dot matrix pattern can be shapes other than circular, such as ovals or rectangles, for example. In addition, the dots can be arranged in patterns other than a regular Cartesian grid, such as following the outline of the stent segment, for example, as suited for a particular application. In one embodiment the first coating section 217 and second coating section 219 are provided in a relatively small scale, having a diameter or width of approximately 1 millimeter (0.03937 inches) and preferably a diameter or width of approximately 0.025 millimeter (0.00098 inches). Moreover, the first coating section 217 and second coating section 219 are further provided in an intermittent manner. As seen in this figure, the intermittent manner includes having a bare or uncoated section 218 of stent disposed between the first coating section 217 and second coating section 219, the bare or uncoated section 218 of stent providing separation between first coating section 217 and second coating section 219 of approximately 1 millimeter (0.03937 inches) and preferably approximately 0.025 millimeter (0.00098 inches) assuming that the stent strut 160 is approximately 0.1016 millimeters (0.004 inches). The exact sizes of coating sections and bare or uncoated sections depends upon the specific drugs and polymers used as well as the overall dimensions of the stent. Finally, it should be understood that section 218 may also be provided in a manner such that section 218 is coated, although without a drug, e.g. coated only with a relatively biologically inert material such as phosphorylcholine, for example.

Figure 6:
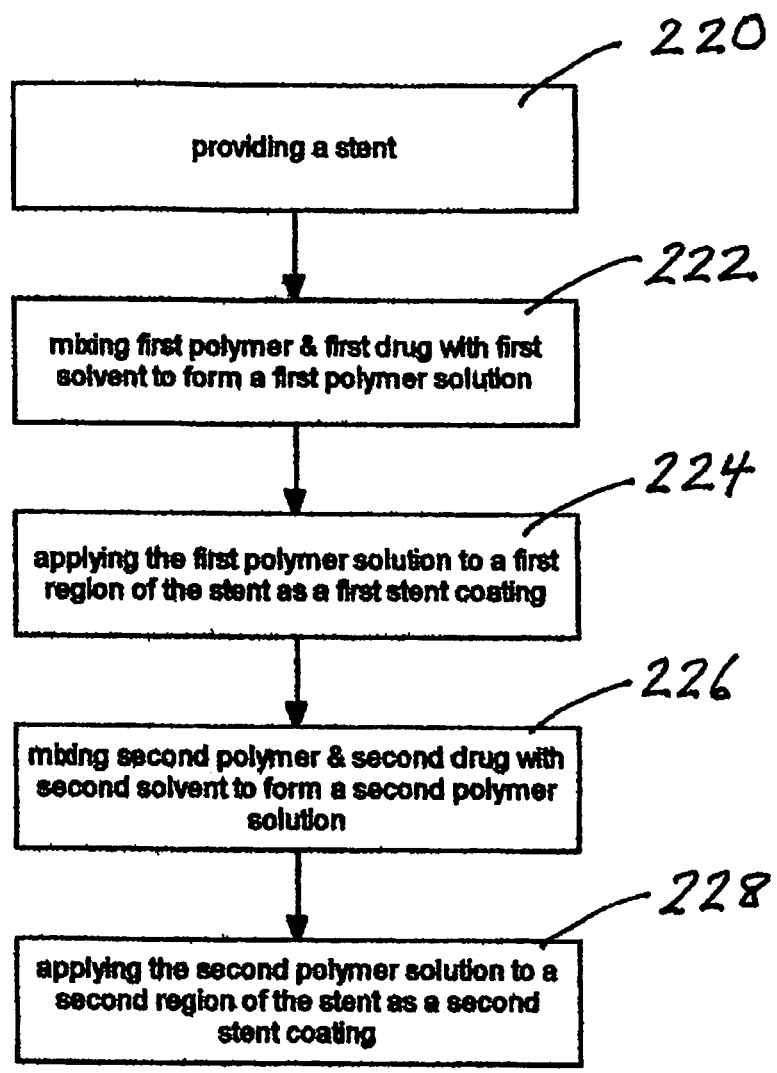
FIG. 6 shows a flow chart of a method of manufacturing a stent having an intermittent coating made in accordance with the present invention.

FIG. 6 shows a flow chart of a method of manufacturing a stent having an intermittent coating made in accordance with the present invention. At 220, a stent is provided. A first polymer and first drug (or other therapeutic agent) are mixed with a first solvent to form a first polymer solution 222, which is applied to a first region of the stent to form a first coating section 224. A second polymer and second drug (or other therapeutic agent) are mixed with a second solvent to form a second polymer solution 226, which is applied to a second region of the stent to form a second coating section 228.

Those skilled in the art will appreciate that the method of manufacturing can be varied for the materials used and the results desired. For certain polymer solutions, a curing step or a drying step for the coating section may be advantageous. In one embodiment, the first drug or second drug can be omitted from the first polymer solution or second polymer solution, respectively, and the coating section provided for mechanical or other properties. In another embodiment, the first polymer solution and the second polymer solution can be applied simultaneously.

Figure 7:
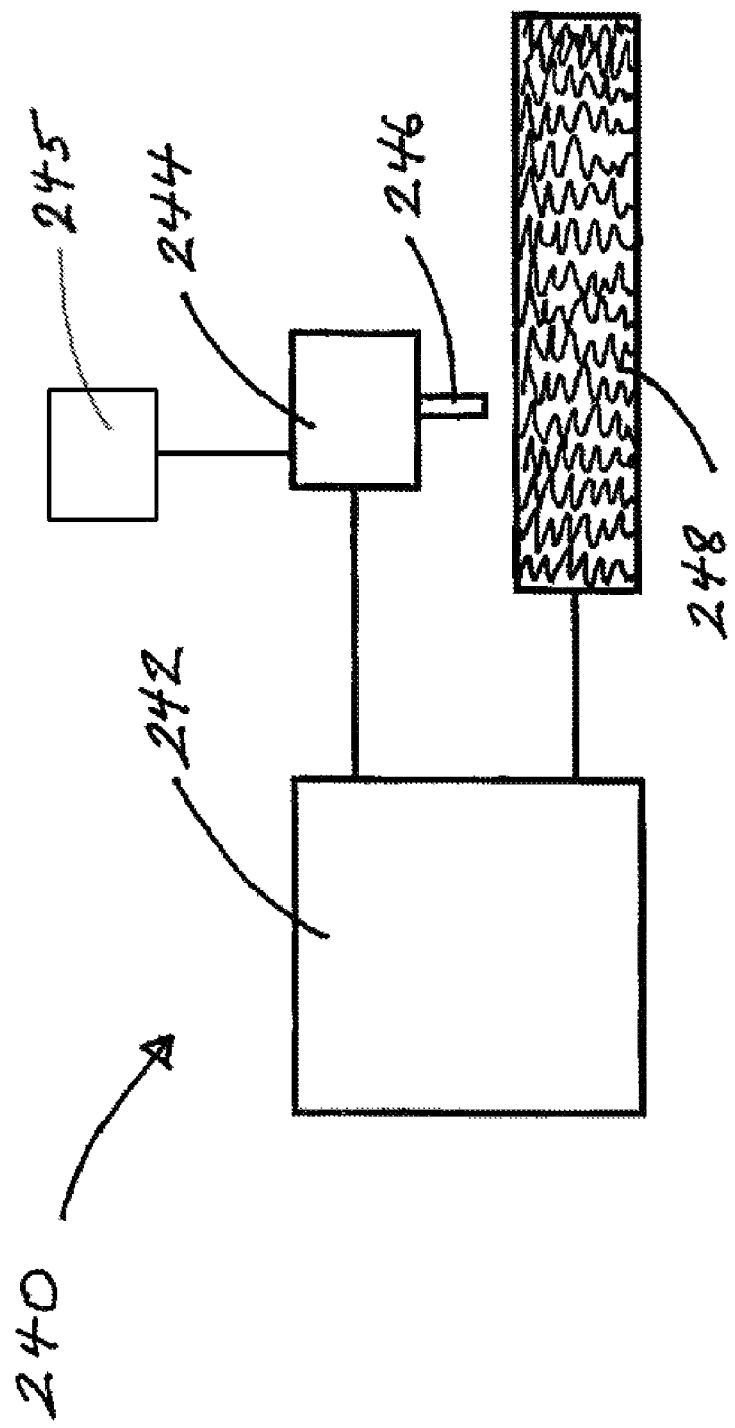
FIG. 7 shows a method of manufacturing a stent made in accordance with the present invention.

FIG. 7 shows a method of manufacturing a stent made in accordance with the present invention. Referring to FIG. 7, a coating fixture 240 holds and controls the position of a stent 248 while the coating section is applied. Typically, the stent 248 can be an uncrimped stent, but the stent can be crimped, or in the expanded or unexpanded condition for a self-expanding stent. The coating fixture 240 comprises a drive 242 and a sprayer 244 having one or more spray heads 246. The one or more spray heads 246 and the sprayer 244 for applying a polymer solution can be fed by a mixer 245 operable to mix a polymer and a therapeutic agent with a solvent to form a polymer solution. The drive 242 controls the relative position between the spray head 246 and the stent 248. The drive 242 can move the stent 248, move the spray head 246, or move both the stent 248 and the spray head 246. In one embodiment, the drive 242 can rotate the stent 248 and can move the spray head 246 axially along the stent 248. The drive 242 can be a computerized numerically controlled machine. The sprayer 244 can have one or more spray heads 246. If a plurality of spray heads is used, more than one polymer solution can be applied to the stent 248 at one time. The sprayer 244 can use micro-sprayer or inkjet technology.

FIG. 7 provides an example using a spray system to apply the coating sections, but many other application systems are possible as will be appreciated by those skilled in the art. The coating sections can also be applied to the stent by dip coating, printing with a roller or a pad, wiping, electrostatic deposition, vapor deposition, epitaxial growth, and combinations thereof Any method producing discrete coating sections can be used, so long as the coating sections produced are substantially separate and the overlap between coating sections is maintained at an acceptable level. Some overlap between coating sections to facilitate manufacturing can be allowed without departing from the spirit of the presently claimed invention.

It is important to note that FIGS. 1-7 illustrate specific applications and embodiments of the present invention, and is not intended to limit the scope of the present disclosure or claims to that which is presented therein. For example, the coating sections can be provided in discrete regions on the inside or the outside diameter, or both as well as provided on differing longitudinal as well as radial sections of the stent. Upon reading the specification and reviewing the drawings hereof, it will become immediately obvious to those skilled in the art that myriad other embodiments of the present invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. A stent delivery system comprising:
a catheter;
a balloon operably attached to the catheter;
a stent disposed on the balloon, the stent having a plurality of end-to-end cylindrical stent segments, the axes of the plurality of cylindrical stent segments lying along a longitudinal axis of the stent, the stent having a first region continuous across at least one pair of longitudinally adjacent cylindrical stent segments and a second region continuous across at least one pair of longitudinally adjacent cylindrical stent segments; and
a coating including a first coating section comprising a first polymer and a second coating section comprising a second polymer, the first polymer being different than the second polymer;
wherein:
the first coating section is a single layer directly adjacent to and completely covering the outer surface in the first region of the longitudinally adjacent cylindrical stent segments; and
the second coating section is another single layer directly adjacent to and completely covering the outer surface in the second region of the longitudinally adjacent cylindrical stent segments; and
the first region and the second region are discrete, and the first coating section and the second coating section are discrete.

2. The stent delivery system of claim 1 wherein the first coating section includes a first therapeutic agent and the second coating section includes a second therapeutic agent.

3. The stent delivery system of claim 1 wherein the first coating section includes a therapeutic agent.

4. The stent delivery system of claim 1 wherein the first region and the second region form a pattern selected from the group consisting of ring patterns, striped patterns, and spotted patterns.

5. A coated stent comprising:
a stent having a plurality of end-to-end cylindrical stent segments, the axes of the plurality of cylindrical stent segments lying along a longitudinal axis of the stent, the stent having a first region continuous across at least one pair of the longitudinally adjacent cylindrical stent segments and a second region continuous across at least one pair of the longitudinally adjacent cylindrical stent segments; and
a coating including a first coating section comprising a first polymer and a second coating section comprising a second polymer, the first polymer being different than the second polymer;
wherein:
the first coating section is a single layer directly adjacent to and completely covering the outer surface in the first region of the longitudinally adjacent cylindrical stent segments; and
the second coating section is another single layer directly adjacent to and completely covering the outer surface in the second region of the longitudinally adjacent cylindrical stent segments; and
the first region and the second region are discrete, and the first coating section and the second coating section are discrete.

6. The coated stent of claim 5 wherein the first coating section includes a first therapeutic agent and the second coating section includes a second therapeutic agent.

7. The coated stent of claim 5 wherein the first coating section includes a therapeutic agent.

8. The coated stent of claim 5 wherein the first region and the second region form a pattern selected from the group consisting of ring patterns, striped patterns, spotted patterns, and spotted patterns.

9. A method for producing a coated stent comprising:
providing a stent having a plurality of end-to-end cylindrical stent segments, the axes of the plurality of cylindrical stent segments lying along a longitudinal axis of the stent, the stent having a first region continuous across at least one pair of longitudinally adjacent cylindrical stent segments and a second region continuous across at least one pair of longitudinally adjacent cylindrical stent segments;
mixing a first polymer and first therapeutic agent with a first solvent to form a first polymer solution;
applying the first polymer solution directly to the stent in the first region to form a first coating section of a coating completely covering the outer surface in the first region of the longitudinally adjacent cylindrical stent segments;
mixing a second polymer and second therapeutic agent with a second solvent to form a second polymer solution; and
applying the second polymer solution directly to the stent in the second region to form a second coating section of the coating completely covering the outer surface in the second region of the longitudinally adjacent cylindrical stent segments,
wherein the first coating section and the second coating section are discrete, and the first region has a longitudinal length greater than the diameter of the stent in an expanded state.

10. The method of claim 9 wherein applying the first polymer solution and applying the second polymer solution further comprises applying the first polymer solution and applying the second polymer solution simultaneously.

11. The method of claim 9 further comprising curing the first polymer solution and curing the second polymer solution.

12. The method of claim 9 wherein applying the first polymer solution to the first region further comprises:
mounting the stent in a coating fixture; and
spraying the first polymer solution on the first region.

13. The method of claim 12 wherein the coating fixture is a computerized numerically controlled machine.

14. The method of claim 12 wherein spraying the first polymer solution on the first region further comprises spraying the first polymer solution by a spraying method selected from the group consisting of micro-spraying and inkjet spraying.

15. The method of claim 9 wherein applying the first polymer solution to the first region further comprises applying the first polymer solution by an application method selected from the group consisting of pad printing, inkjet printing, rolling, painting, spraying, micro-spraying, dipping, wiping, electrostatic deposition, vapor deposition, epitaxial growth, and combinations thereof.

16. A system for producing a coated stent from a stent having a plurality of end-to-end cylindrical stent segments, the axes of the plurality of cylindrical stent segments lying along a longitudinal axis of the stent, the stent having a first region continuous across at least one pair of the longitudinally adjacent cylindrical stent segments and a second region continuous across at least one pair of the longitudinally adjacent cylindrical stent segments, comprising:
means for mixing a first polymer and first therapeutic agent with a first solvent to form a first polymer solution;
means for applying the first polymer solution directly to the stent in the first region to form a first coating section of a coating completely covering the outer surface in the first region of the longitudinally adjacent cylindrical stent segments;
means for mixing a second polymer and second therapeutic agent with a second solvent to form a second polymer solution; and
means for applying the second polymer solution directly to the stent in the second region to form a second coating section of the coating completely covering the outer surface in the second region of the longitudinally adjacent cylindrical stent segments,
wherein the first coating section and the second coating section are discrete, and the first region has a longitudinal length greater than the diameter of the stent in an expanded state.

17. The system of claim 16 wherein means for applying the first polymer solution and means for applying the second polymer solution further comprises means for applying the first polymer solution and the second polymer solution simultaneously.

18. The system of claim 16 further comprising means for curing the first polymer solution and means for curing the second polymer solution.

19. The system of claim 16 wherein means for applying the first polymer solution to the first region further comprises:
means for mounting the stent in a coating fixture; and
means for spraying the first polymer solution on the first region.

20. A coated stent comprising:
a stent having a plurality of end-to-end cylindrical stent segments, the axes of the plurality of cylindrical stent segments lying along a longitudinal axis of the stent, the stent having a discrete first region continuous across at least one pair of the longitudinally adjacent cylindrical stent segments and a discrete second region continuous across at least one pair of the longitudinally adjacent cylindrical stent segments;
a first polymer including a first therapeutic agent, the first polymer being directly adjacent to and completely covering the outer surface in the discrete first region of the longitudinally adjacent cylindrical stent segments as a first coating section of a coating; and
a second polymer including a second therapeutic agent, the second polymer being directly adjacent to and completely covering the outer surface in the discrete second region of the longitudinally adjacent cylindrical stent segments as a second coating section of the coating, the first polymer being different than the second polymer,
wherein the first coating section and the second coating section are discrete, and the discrete first region has a longitudinal length greater than the diameter of the stent in an expanded state.

21. The coated stent of claim 20 wherein the discrete first region and the discrete second region are separated by a bare section on the outer surface of the stent.

22. The coated stent of claim 21 wherein the bare section extending between the discrete first region and the discrete second region for a distance of approximately 1 millimeter (0.03937 inches).

23. The coated stent of claim 22 wherein the bare section extending between the discrete first region and the discrete second region for a distance of approximately 0.025 millimeter (0.00098 inches).

* * * * *